(12) United States Patent
Connelly, Jr.

(10) Patent No.: US 7,309,444 B2
(45) Date of Patent: Dec. 18, 2007

(54) LAYERED TABLET WATER TREATMENT COMPOSITIONS AND METHOD OF USE

(75) Inventor: Thomas V. Connelly, Jr., Kirkwood, MO (US)

(73) Assignee: Stellar Technology Company, Sauget, IL (US)

( * ) Notice: Subject to any disclaimer, the term of this patent is extended or adjusted under 35 U.S.C. 154(b) by 333 days.

(21) Appl. No.: 10/906,024

(22) Filed: Jan. 31, 2005

(65) Prior Publication Data
US 2005/0173353 A1 Aug. 11, 2005

Related U.S. Application Data

(63) Continuation-in-part of application No. 10/064,929, filed on Aug. 29, 2002, now Pat. No. 6,852,238.

(51) Int. Cl.
C02F 1/76 (2006.01)
C01B 7/00 (2006.01)

(52) U.S. Cl. .................... 210/753; 252/175

(58) Field of Classification Search ........ 210/753–756, 210/169, 198.1; 422/37; 252/75, 187.1, 252/175; 510/224, 225; 424/464, 472, 661, 424/665
See application file for complete search history.

(56) References Cited

U.S. PATENT DOCUMENTS

| | | | |
|---|---|---|---|
| 3,873,685 A | 3/1975 | Kibbel, Jr. et al. | |
| 4,828,745 A | 5/1989 | Jeschke et al. | |
| 4,846,979 A | 7/1989 | Hamilton | |
| 5,133,892 A | 7/1992 | Chun et al. | |
| 5,240,713 A | 8/1993 | Ayer | |
| 5,283,065 A | 2/1994 | Doyon et al. | |
| 5,407,598 A * | 4/1995 | Olson et al. | 252/186.35 |
| 5,549,913 A | 8/1996 | Colombo et al. | |
| 5,700,377 A | 12/1997 | Cox | |
| 5,738,874 A | 4/1998 | Conte et al. | |
| 5,783,540 A | 7/1998 | Secemski et al. | |
| 5,837,663 A | 11/1998 | Nicholson et al. | |
| 5,962,387 A | 10/1999 | Gorlin et al. | |
| 6,083,533 A | 7/2000 | Cremer | |
| 6,136,344 A | 10/2000 | Depui et al. | |
| 6,149,821 A * | 11/2000 | Rounds et al. | 210/754 |
| 6,149,940 A | 11/2000 | Maggi et al. | |
| 6,183,778 B1 | 2/2001 | Conte et al. | |
| 6,183,845 B1 | 2/2001 | Ikemoto | |
| 6,194,368 B1 | 2/2001 | Waschenbach et al. | |
| 6,589,925 B1 * | 7/2003 | Binstock et al. | 510/224 |
| 2005/0040116 A1 * | 2/2005 | Purdy et al. | 210/749 |
| 2006/0293178 A1 * | 12/2006 | Martin | 502/321 |

* cited by examiner

*Primary Examiner*—Frank M. Lawrence
(74) *Attorney, Agent, or Firm*—Blackwell Sanders LLP

(57) ABSTRACT

The present invention relates generally to novel water treatment compositions. More particularly, the invention relates to solid water treatment compositions in the form of a water soluble tablet containing at least one halogen source and at least a pH compensating source in a layered tablet in which each of layer is configured to be simultaneously exposed to the water being treated and wherein one layer comprises the halogen source and another layer comprises a pH compensating source. Methods for controlling water biofouling and disinfecting water systems, particularly swimming pools and spas, are disclosed.

39 Claims, 1 Drawing Sheet

LAYERED TABLET WATER TREATMENT COMPOSITIONS AND METHOD OF USE

CROSS-REFERENCE TO RELATED APPLICATIONS

This application is a continuation-in-part of U.S. patent application Ser. No. 10/064,929, filed Aug. 29, 2002, which is now issued as U.S. Pat. No. 6,852,238, issued on Feb. 8, 2005, incorporated herein by reference.

BACKGROUND OF THE INVENTION

The provision of safe and clean water that is also visually attractive to the user is important in municipal, industrial, and recreational applications. Conventional water treatments employ physical, chemical, and biological processes either alone or in combination to produce water of acceptable quality.

In applications where water is intended for human contact or consumption, the water must be treated so that it is aesthetically pleasing in terms of taste, color, turbidity, odor, and pH, environmentally safe, and effectively free of pathogens and chemicals responsible for both acute and chronic illness. Conventional methods use chemicals as oxidizers, biocides, algaecides, and pH buffers for the treatment of water. Typically, the chemicals are added to the water separately as part of an overall water maintenance or purification program. The water is monitored on an hourly, daily, or weekly basis, and when a particular treatment parameter is not acceptable or in compliance with regulatory levels, the appropriate amount of the necessary chemical is added. Often, treatment of one water quality parameter causes another water quality parameter to change. Conventional treatment, therefore, employs a continuous balancing process of monitoring water quality parameters and dosing with various chemicals to create and to maintain the appropriate water quality.

It must be appreciated that potable water typically has a pH of 8.3 with a total alkalinity of 50 ppm and a calcium content of 100 ppm. The term "total alkalinity" is used to describe the total amount of dissolved alkaline substances in water, excluding calcium. "Dissolved solids" in suspension in swimming pool water, predominantly provided by the total alkalinity and calcium in the water, give the water its "blue" color when sunlight reflects off the water. Thus, reductions in the amount of dissolved solids in water will result in the water having an increasingly green color. It will be appreciated that it is desirable to provide a water purification composition that provides sufficient dissolved solids to give the water a blue color.

In applications such as swimming pools and spas, chemical combinations attempt to provide a complete water quality treatment. For example, U.S. Pat. No. 5,700,377, issued to Cox on Dec. 23, 1997, discloses a complete treatment for the purification of water in non-porous swimming pools, obviating the need for the addition of any other compounds to the water. The chemical composition of Cox includes a peroxide compound, an ammonium-based biocidal compound, an acidic compound, a basic compound, a calcium-releasing basic compound, and EDTA in the form of a "kit" or mixture. The composition is added to the water when the pH of that water is outside the human comfort zone of 7.2 to 7.6 in order to bring the pH within the zone range. Therefore, water clarification is combined with a pH adjustment. However, the use of such mixtures exposes the user to the disadvantage of maintaining the mixture in a condition that prohibits the reaction of the basic material with the acidic materials. Also, such reaction occurs upon addition of the mixture to the water being treated.

Attempts to combine various chemicals into a convenient tablet form have been known. Tabletting of various chemicals for release at various times has been used extensively in the administration of medicine. Typical examples of such tablets are found in U.S. Pat. No. 6,183,778 issued to Conte et al. on Feb. 6, 2001; U.S. Pat. No. 6,149,940 issued to Maggi et al. on Nov. 21, 2000; U.S. Pat. No. 6,136,344 issued to Depui et al. on Oct. 24, 2000; and U.S. Pat. No. 6,083,533 issued to Cremer on Jul. 4, 2000. It can be appreciated that time release of medicaments has great value in treatment regimens and tablets that provide such properties are numerous. The above list is a mere sample of those references wherein tablets contain various layers having different solubility rates in digestive fluids.

Another industry finding great utility with multi-layered tablets having various components for differing purposes is the automatic dishwashing detergent industry. There, the advantage of various wash cycles of automatic dishwashers provide an opportunity to build a multi-layer tablet wherein several agents are combined in a layered fashion to supply the appropriate cleaning chemical at the propitious time in the wash cycle. A typical example of such disclosures are U.S. Pat. No. 6,194,368, issued to Waschenbach et al. on Feb. 27, 2001, wherein the first layer of a dishwashing detergent tablet contains an activated, halogen-free bleach, and silver/copper corrosion inhibitor in an outer layer and a bleach activator in another layer. U.S. Pat. No. 5,962,387, issued to Gorlin et al. on Oct. 5, 1999, discloses a three-layer tablet wherein each layer contains a different detergent formulation. As the wash cycle proceeds, a different formulation believed optimum for each portion of the cycle is exposed. In U.S. Pat. No. 5,837,663, issued to Nicholson et al. on Nov. 17, 1998, there is disclosed a two-layer tablet for automatic dish washing where a first layer contains a buffer, a builder and an enzyme which dissolves at a pH of 9-11. A second layer is provided containing a peracid and an acidity agent having a melting point of from 35 to 50 degrees C. along with a carrier. The second layer delivers a pH of from 6.5-9. The release order is said to allow optimum removal of stains and food from the dishes. Another example of a multi-layer tablet for use in automatic dishwashers allowing for different pH levels during a single wash cycle appears in U.S. Pat. No. 5,783,540, issued to Secemski et al. on Jul. 21, 1998. In this patent, an oxygen bleach, a buffer system to deliver a pH of 8.5-11, a builder and an enzyme are contained in one layer while a second layer is provided containing an acidity agent to provide a pH below 9, a carrier having a high melting point for the acidity agent and an anti-scaling agent. In theory, the high melting carrier is dispersed in the high temperature final rinse cycle thereby providing a superior finish to the articles, especially glass. Other examples of multi-layer tablets used in automatic dish washing machines are found in U.S. Pat. No. 5,549,913 issued to Colombo et al. on Aug. 27, 1996; U.S. Pat. No. 5,133,892 issued to Chun et al. on Jul. 28, 1992; and U.S. Pat. No. 4,828,745 issued to Jeschke et al. on May 9, 1989.

The use of tablets for administering halogen-containing chemicals to swimming pools has long been known. Usually the tablets are placed in the pool water system at points where flowing water is provided such as in the filtration system skimmer or in a floating basket at the surface of the pool. As noted above, in most instances, the condition of the pool water is monitored periodically to insure a desirable pH level, as well as desirable algaecide, alkalinity, and hardness control is maintained while administering a generally acid contributing halogen containing compound. A two-layer tablet for chlorination of water systems is disclosed in U.S. Pat. No. 3,873,685 issued to Kibbel, Jr. et al. on Mar. 25, 1975. This patent discloses the combination of contiguous layers in one tablet wherein one layer contains a fast dissolving halogen-releasing agent while a second layer provides a slower dissolving halogen-releasing agent. A relatively fast dissolving halogen-releasing agent, sodium dichloroisocyanurate dihydrate is contained in one discrete layer and trichloroisocyanuric acid is contained in another layer. Various geometric shapes of tablets are suggested wherein the discrete portions of the ingredients are provided in structures having either a layered structure or an inner core and outer core such as in the shape of a rod or oval ball. While providing a measure of convenience in placing halogen-releasing materials in the water, the need still arises to monitor and control the total alkalinity of the water as well as the pH level, particularly in swimming pools.

Because of the proximity of reactive chemicals such as an acidic material and a basic material to each other is a single composition, the production of such products have proven to have limited or no commercial value because of the danger presented by the possibility of an exothermic reaction occurring during storage and shipping of large quantities of such materials.

SUMMARY OF THE INVENTION

The present invention relates generally to water treatment compositions and methods of use. More particularly, the invention relates to solid water treatment compositions comprising a halogen source and a pH compensating source and methods of using such compositions. In preferred embodiments of the invention, solid water treatment compositions are provided and utilized which simultaneously release active components in non-encapsulated tablet form.

A safe and effective combination of a halogen source with a pH compensating source has now been discovered in the creation of a multi-layered tablet. The water treatment composition of this invention comprises a multi-layer tablet wherein one discrete layer contains at least one halogen source and a second discrete layer contains at least a pH compensating source. Preferably, these layers are configured to be simultaneously exposed to the water being treated. Materials useful in this invention are solid, particulate materials capable of being compressed into separate, contiguous layers providing a structurally strong, storage-stable tablet. The ratio of the amount of halogen source to the amount of pH compensating source is adjusted to provide, when dissolved in a water system, a pH of from 7.2-7.8 and total alkalinity of from 80 to 150 ppm, depending upon the materials of construction of the pool, spa or other form of containment of the water to be treated. Such amounts can be calculated as will be demonstrated below. The multi-layered tablets are conveniently prepared by known methods of tablet formation.

There is also provided in accordance with this invention, a method of administering a biocidal amount of a halogen source to a water system while simultaneously adjusting the pH and total alkalinity of the water by means of adding to the water a tablet of this invention containing both a halogen source and an alkaline source in discrete, contiguous layers in a single tablet that dissolves in the water system. It has been discovered that the layered tablet configuration provides separated surfaces of a stable tablet from which each layer is able to dissolve in the water at a rate of dissolution substantially independent of the other layer. Minimal direct reaction occurs between the materials in the separate layers as they separately dissolve providing the needed biocidal action while also providing compensating alkalinity.

The solid water treatment tablets of this invention may also comprise excipients and other inert or active additives, including but not limited to scale inhibitors (such as organic phosphonic acids or phosphonates), clarifiers (such as ethylene diamine tetra acetic acid "EDTA") and algaecides (such as copper sulfate or quaternary ammonium compounds).

DETAILED DESCRIPTION OF THE INVENTION

Figure 1:
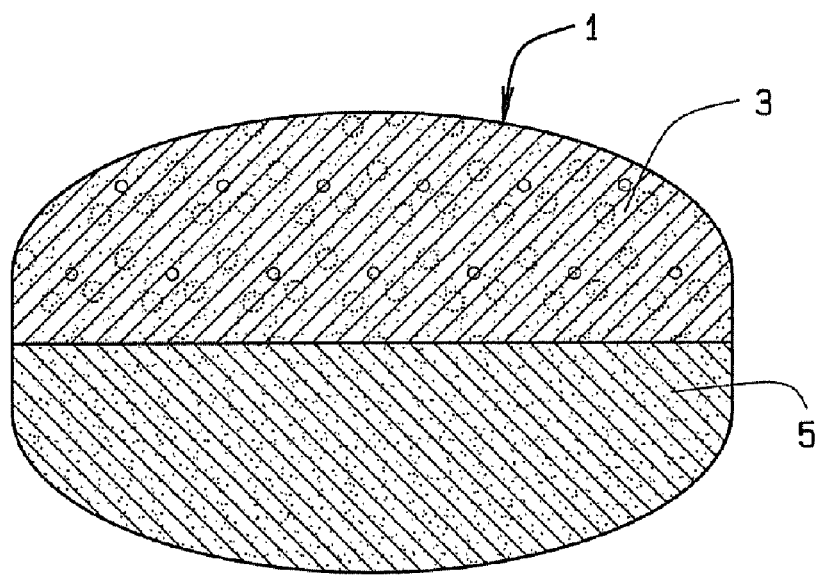
FIG. 1 shows a typical two-layer tablet of this invention, wherein tablet 1 provides a halogen source layer 3 and a pH compensating source layer 5. As noted above, the two separate layers embodied in a structurally stable tablet maintains the two layers separate and apart during dissolution in the aqueous medium. Such separation is a large factor in the element of safety, not only during actual use but also during shipping and storage of the tablet.

The water treatment composition of this invention comprises a tablet containing at least two contiguous layers, one layer comprising at least one halogen source and a second layer comprising at least one pH-compensating source. It has been discovered that, with usual precautions to prevent contamination with water and water bearing substances, the tablets of this invention are stable. Surprisingly, each layer of the inventive tablet dissolves at a rate that is dependent upon the properties of each layer separate and apart from the other layer.

As employed in this invention, the term "water system" means a defined quantity of water contained in a vessel such as a swimming pool, spa, industrial cooling system, pond, fountain, etc.

As employed in this invention, the term "inert" means a material that is non-reactive with a halogen source of a pH compensating source.

As used herein, the "at least one halogen source" comprises one or more compounds that provide hypohalous acid, HOX or hypohalite ion, or OX species wherein X is halogen when dissolved in water.

As used herein, the term "alkaline source" refers to compounds containing metal cations within group IA and IIA referenced in the periodic table. In particular, this includes cations of the alkali metals lithium, sodium, potassium, rubidium, and cesium; and further includes cations of the alkaline earth metals beryllium, magnesium, calcium, strontium, and barium in compounds providing, in aqueous solution, a pH above 7. Typical compounds usable as an alkaline source in this invention include: alkaline hydroxides; alkaline carbonates; alkaline bicarbonates; alkaline phosphates; alkaline silicates; and alkaline borates. Particularly preferred alkaline sources are sodium carbonate and sodium bicarbonate.

As employed herein, the term "basic in aqueous solution" means a material that, alone in aqueous solution, provides a pH above 7.

As employed herein, the term "acid in aqueous solution" means a material that, alone in aqueous solution provides a pH below 7.

Typical halogen sources may comprise any halogen-containing compound that provides a halogen ion in aqueous solution. Halogen ions such as chlorine, bromine, and iodine may be particularly useful. Preferably, the halogen source comprises chlorine or bromine or a combination thereof. Representative halogen sources, for example, include trichloroisocyanuric acid (TCCA), dichloroisocyanuric acid (DCCA), monochloroisocyanuric acid, potassium dichloroisocyanuric acid, sodium dichloroisocyanuric acid dihyrate, anhydrous sodium dichloroisocyanuric acid, tribromoisocyanuric acid, dibromoisocyanuric acid, monobromoisocyanuric acid, monobromodichloroisocyanuric acid, dibromomonochloroisocyanuric acid, calcium hypochlorite, sodium hypochlorite, lithium hypochlorite, 1,3-dichloro-5,5-dimethylhydantoin (DCDMH), 1,3-dibromo 5,5-dimethylhydantoin, 1-bromo-3-chloro-5,5-dimethylhydantoin (BCDMH), 1-bromo-3-chloro-5-methyl-5-ethylhydantoin (BCEMH), 1,3-dichloro-5-methyl-5-ethylhydantoin, 1,3-dichloro-5,5-dimethylhydantoin, 1,3-dibromo-5,5-dimethyhydantoin, trichloromelamine, tribromomelamine and mixtures thereof. The halogen source may further comprise one mole of trichloroisocyanuric and four moles of potassium dichloroisocyanuric acid or four moles of sodium dichloroisocyanuric acid; compositions comprising trichloroisocyanuric acid and potassium bromide; and compositions comprising about 60% by weight 1-bromo-3-chloro-dimethylhydantoin, about 30% by weight 1,3-dichloro-5,5-dimethylhydantoin and about 10% by weight 1,3-dichloro-5-ethyl-5-methylhydantoin.

Halogen sources are readily available in commercial form. The most preferred halogen source is TCCA and DCCA. Other preferred halogen sources are BCDMH, DCDMH, BCEMH and 1,3-Dibromo-5,5-dimethylhydantoin (DBDMH).

Solid forms of the halogen source and water treatment composition can be blended powders, compressed granules, briquettes, pellets, extrusions, agglomerations, flakes, sheets, cast blocks, compressed blocks and the like.

The pH-compensating source employed in the layered tablet of this invention is any solid, compactable material soluble in aqueous media to provide a pH-compensating source in the water. Of course, where water is intended for human contact or consumption, the pH-compensating source must be non-toxic at concentrations adequate to provide the pH and total alkalinity totals noted above.

Typical alkaline sources include alkali metal or alkaline earth carbonates, alkaline or alkaline earth bicarbonate, an alkaline phosphate, an alkaline silicate, an alkaline borate, and mixtures of these compounds. More particularly, preferred alkaline sources useful in this invention include sodium carbonate, potassium carbonate, lithium carbonate, sodium bicarbonate, potassium bicarbonate and lithium bicarbonate. Typical acidic pH materials (where the halogen source contributes basic pH to the water) include sodium bisulfate or a combination of soot ash and sodium bicarbonate.

In the water treatment method of this invention the one or more layered tablets as described above are inserted into the water body to be treated whereby the layers of the tablet simultaneously dissolve at independent rates. Generally the alkaline source layer will dissolve at a faster rate than the halogen source layer.

Proper water balance for pools and spas means maintaining pH, total alkalinity, calcium hardness and temperature in ranges that will make the water neutral so as to avoid a tendency to either corrode or to scale. The proper range for these parameters is generally as follows:

TABLE 1

| | |
|---|---|
| pH | 7.2-7.6 |
| Total Alkalinity | 80-120 ppm for plaster pools |
| | 100-150 ppm for Vinyl and Painted pools |
| Calcium Hardness | 90-275 |
| Temperature | 76-84° F. for Pools |
| | 95-104° F. for Spas |

Calcium hardness for a tablet can range from about 90 to about 275 with a preferred range of about 141 to about 200 and a most preferred range from about 200 to about 275 and higher. The density for a tablet can range from about 1.3 grams per cubic centimeter (81.15 pounds per cubic foot) to about 1.5 grams per cubic centimeter (93.63 pounds per cubic foot) with a preferred range from about 1.51 grams per cubic centimeter (94.26 pounds per cubic foot) to about 1.7 grams per cubic centimeter (106.12 pounds per cubic foot) with a most preferred range of 1.71 grams per cubic centimeter (106.74 pounds per cubic foot) to about 2.1 grams per cubic centimeter (131.09 pounds per cubic foot).

Various chlorine sources and pH compensating sources are employed in the layered tablet and process of this invention. Typical materials and the effect such material have on a body of water being treated are listed below in Table 2 wherein the following abbreviations are employed:

TCCA: trichloroisocyanuric acid
SDCCA: sodium dichloroisocyanuric acid
Hypo: Hypochlorite
BCDMH: 1-bromo-3-chloro-5,5-dimethylhydantoin
BCEMH: 1-bromo-3-chloro-5-methyl-5-ethylhydantoin
DBDMH: 1,3-dibromo-5,5-dimethylhydantoin

TABLE 2

| Halogen Compound | TCCA | SDCCA | Cal Hypo | Lithium Hypo | BCDMH | BCEMH | DBDMH |
|---|---|---|---|---|---|---|---|
| Chemical State | Solid | Solid | Solid | Solid | Solid | Solid | Solid |
| Typical Effect | Lowers pH 2.9 | Negligible pH 6.0 | Raises pH 11.7 | Raises pH 10.5 | Lowers pH x | Lowers pH 3.6 | Lowers pH x |
| Relative Solubility | Slow | Very Fast | Fast | Very Fast | Slow | Slow | Slow |
| To Re-Adjust pH | Add Base | +Minor Base | Add Acid | Add Acid | Add Base | Add Base | Add Base |

From the above it can be seen that the layered tablet of this invention may contain either a base or an acid depending upon the effect on pH of the halogen source. All of the solid forms above can be tabletted in order to prolong the life of the product. As a practical matter, the solid halogen compounds that dissolve "very fast" are employed differently than those having a slower dissolution rate. For example, SDCCA would only last minutes while the powdered or granular form would last only a few seconds in the solid state when placed in water. A tablet of SDCCA would have utility as a "unit dose" for quick action rather than for any extended treatment period as would other layered tablets of this invention.

The halogen sources of this invention may be mixed and mixtures of these compounds compacted or formed into a layer tablet of this invention. Accordingly, mixtures of any of the halogen sources noted above, TCCA, BCDMH, BCEMH, DBDMH may be combined in measured ratios and compacted into one of the layers of the layered tablet of this invention. The calculated increase or decrease of pH contributed by the halogen source is off-set with an appropriate amount of acid or base material in the other layer in order to maintain the proper water pH balance thereby providing water that does not corrode or scale.

Figure 2:
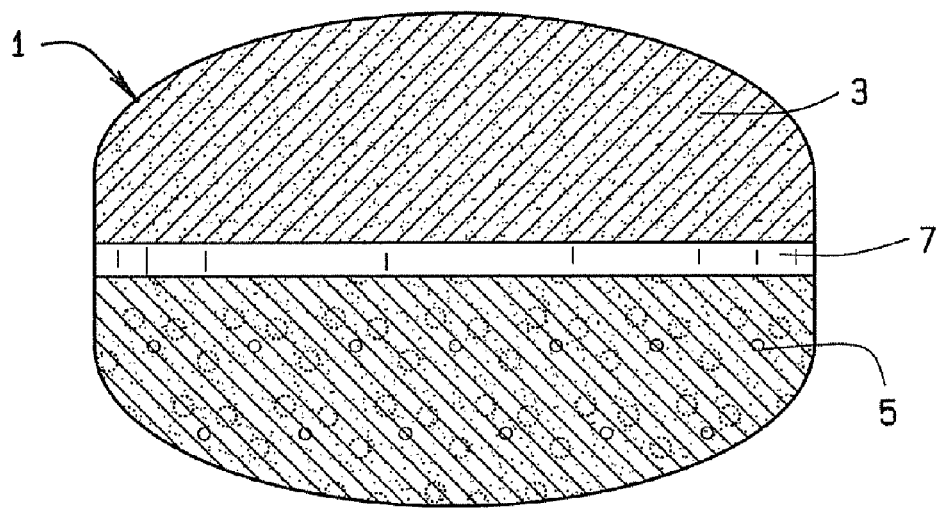
FIG. 2 shows a typical three-layer tablet of this invention, wherein an inert boundary layer 7 is included in the tablet to physically separate the layer containing the halogen source 3 from the layer containing the pH-compensating source 5.

As shown in FIGS. 1 and 2, the acids and bases must be added separately since intimate mixtures of either acids or bases with a given halogen compound will destroy the integrity of the tablet and the advantage of slow solubility. A boundary layer may be employed when a particular combination of halogen source and pH compensating source is desirably maintained apart during manufacture, shipping, storage and use. Preferably, the boundary layer is provided so that it will not prevent the discrete layer containing the halogen source and the discrete layer containing the pH compensating source from being simultaneously exposed to the water to be treated therewith. Any suitable boundary material may be employed and is generally one that is non-reactive to either the halogen source or the pH compensating source and also is neutral in water solution (no effect on pH). As is usual in water treatment materials, the inert boundary layer also is not harmful to humans or construction material holding the treated water. Examples of suitable boundary (barrier) materials include members of the alkali metal salts family such as, but not limited to sodium chloride, sodium sulfate, sodium tripolyphosophate or sodium bicarbonate.

The ratio of halogen source to pH compensating source may vary widely. Because water quality varies widely the ratio of halogen source to pH compensating source can be tailored to the water quality in various areas of the country. For example, the amount of pH compensating source may vary from as little as 5% by weight to about 50% by weight of the halogen source. Adjusting the ratio of each component of the layered tablet of this invention will enable the operator of the water system to balance the water with respect to total alkalinity and pH while maintaining proper halogen content to prevent deterioration of water quality due to impurities.

Presses that can be utilized to create the tablets include, but are not limited to: Baldwin, (Press Models 20, 75A, 45, 45A, 200 and 200A), which are no longer being manufactured but can be purchased from previously-owned equipment vendors: Stokes, (Press Models R, R4, 294, 280g, s5, 210 and Summit™), manufactured by Elizabeth Carbide Die Company Incorporated, having a place of business at 601 Linden Street, McKeesport, Pa. 15132; Korsch America, Inc., (Press Models TRP 900, EK4 and EK5), having a place of business at 18 Bristol Drive, South Easton, Mass. 02375; Courtoy N.V., (Press Models R5 and 46), having a place of business at Bergensesteenweg 186, 1500 Halle, Belgium; Vector, (Press Model Gladiator), having a place of business at 675 44$^{th}$ Street, Marion, Iowa 52302; Dorst America Incorporated, having a place of business at 64 S. Commerce Way, Bethlehem, Pa. 18017; Hydramet America Incorporated, having a place of business at 4605 Delemere Blvd., Royal Oak, Mich. 48073; Kux Manufacturing, having a place of business at 12675 Burt Road, Detroit, Mich. 48223; and Pasadena Hydraulics Incorporated, (Press Model PHI B-23), having a place of business at 14955 Salt Lake Avenue, City of Industry, Calif. 91746.

The amount of pressure applied to each individual tablet can range from about 9.07 metric tons (10 short tons) to about 181.44 metric tons (200 short tons) per tablet with a preferred range of pressure from about 31.75 metric tons (35 short tons) to about 45.36 metric tons (50 short tons) and a most preferred amount of pressure being 36.29 metric tons (40 short tons).

EXAMPLE

Layered tablets of this invention were prepared by supplying a halogen source to the cavity of a stainless steel dye of a Korsch Model TRP 900 Laboratory Hand Press. Then, a pH-compensating source was supplied uniformly on top of the halogen source in the same dye cavity. A tabletting force of 200,000 Newtons (44,961.79 pounds) was applied to the layered materials by means of a mating stainless steel plunger. The hardness is over 200.

What is claimed is:

1. A solid, multi-layer water treatment tablet comprising one discrete layer containing at least one halogen source and a second discrete layer containing at least one pH compensating source, said layers each being configured to be simultaneously exposed to an aqueous solution and wherein the halogen source is acid in an aqueous solution and the pH compensating source is basic in aqueous solution, said layers each being configured to be simultaneously exposed to said aqueous solution.

2. A solid, multi-layer water treatment tablet comprising one discrete layer containing at least one halogen source and a second discrete layer containing at least one pH compensating source, wherein the halogen source is acid in an aqueous solution and the pH compensating source is basic in aqueous solution, said layers each being configured to be simultaneously exposed to said aqueous solution and wherein the halogen source is selected from the group consisting of trichloroisocyanuric acid, dichloroisocyanuric acid, monochloroisocyanuric acid, potassium dichloroisocyanuric acid, sodium dichloroisocyanuric acid dihyrate, anhydrous sodium dichloroisocyanuric acid, tribromoisocyanuric acid, dibromoisocyanuric acid, monobromoisocyanuric acid, monobromodichloroisocyanuric acid, dibromomonochloroisocyanuric acid, sodium hypochlorite, calcium hypochlorite, lithium hypochlorite, 1,3-dichloro-5,5-dimethylhydantoin, 1,3-dibromo 5,5-dimethylhydantoin, 1-bromo-3-chloro-5,5-dimethylhydantoin, 1,3-dichloro-5-methyl-5-ethylhydantoin, 1,3-dichloro-5, 5-dimethylhydantoin, 1,3-dibromo-5,5-dimethylhydantoin, trichloromelamine, tribromomelamine and mixtures thereof and the pH compensating source is selected from the group consisting of alkali metal or alkaline earth carbonates, alkaline or alkaline earth bicarbonates, an alkaline phosphate, an alkaline silicate, an alkaline borate and mixtures thereof.

3. The tablet of claim 2, wherein the alkali metal carbonate includes sodium carbonate.

4. The tablet of claim 2, wherein the alkali metal bicarbonate includes sodium bicarbonate.

5. The tablet of claim 2, wherein the pH compensating source comprises from about 5% to about 50%, by weight, of the halogen source.

6. The tablet of claim 2, wherein the halogen source comprises one mole of trichloroisocyanuric and four moles of sodium dichloroisocyanuric acid.

7. The tablet of claim 2, wherein the halogen source comprises one mole of trichloroisocyanuric and four moles of potassium dichloroisocyanuric acid.

8. The tablet of claim 2, wherein the halogen source comprises about 60% by weight 1-bromo-3-chloro-dimethylhydantoin, about 30% by weight 1,3 dichloro 5,5-dimethylhydantoin and about 10% by weight 1,3-dichloro-5-ethyl-5-methylhydantoin.

9. The tablet of claim 2, wherein the halogen source is calcium hypochlorite, sodium hypochlorite, lithium hypochlorite, or mixtures thereof.

10. A method of treating a water system, which comprises adding to the water a solid, multi-layer water treatment tablet comprising one discrete layer containing at least one halogen source and a second discrete layer containing at least one pH compensating source, said layers each being configured to be simultaneously exposed to an aqueous solution and wherein the halogen source is acid in an aqueous solution and the pH compensating source is basic in aqueous solution, wherein the halogen source is selected from the group consisting of trichloroisocyanuric acid, dichloroisocyanuric acid, monochloroisocyanuric acid, potassium dichloroisocyanuric acid, sodium dichloroisocyanuric acid dihyrate, anhydrous sodium dichloroisocyanuric acid, tribromoisocyanuric acid, dibromoisocyanuric acid, monobromoisocyanuric acid, monobromodichloroisocyanuric acid, dibromomonochloroisocyanuric acid, 1,3-dichloro-5, 5-dimethylhydantoin, 1,3-dibromo 5,5-dimethylhydantoin, 1-bromo-3-chloro-5,5-dimethylhydantoin, 1,3-dichloro-5-methyl-5-ethylhydantoin, 1,3-dichloro-5, 5-dimethylhydantoin, 1,3-dibromo-5,5-dimethylhydantoin, 1,3-dibromo-5,5-dimethylhydantoin, trichloromelamine, tribromomelamine and mixtures thereof and the pH compensating source is selected from the group consisting of alkali metal or alkaline earth carbonates, alkaline or alkaline earth bicarbonates, an alkaline phosphate, an alkaline silicate, an alkaline borates and mixtures thereof.

11. The method of claim 10, wherein the alkali metal carbonate includes sodium carbonate.

12. The method of claim 10, wherein the alkali metal bicarbonate includes sodium bicarbonate.

13. The method of claim 10, wherein the pH compensating source includes from about 5% to about 50%, by weight, of the halogen source.

14. A solid, multi-layer water treatment tablet comprising one discrete layer containing at least one halogen source and a second discrete layer containing at least one pH compensating source, wherein the halogen source is acid in an aqueous solution and the pH compensating source is basic in aqueous solution, said layers each being configured to be simultaneously exposed to said aqueous solution and wherein the halogen source is selected from the group consisting of trichloroisocyanuric acid, dichloroisocyanuric acid, monochloroisocyanuric acid, potassium dichloroisocyanuric acid, sodium dichloroisocyanuric acid dihyrate, anhydrous sodium dichloroisocyanuric acid, tribromoisocyanuric acid, dibromoisocyanuric acid, monobromoisocyanuric acid, monobromodichloroisocyanuric acid, dibromomonochloroisocyanuric acid, 1,3-dichloro-5, 5-dimethylhydantoin, 1,3-dibromo 5,5-dimethylhydantoin, 1-bromo-3-chloro-5,5-dimethylhydantoin, 1,3-dichloro-5-methyl-5-ethylhydantoin, 1,3-dichloro-5, 5-dimethylhydantoin, 1,3-dibromo-5,5-dimethylhydantoin, trichloromelamine, tribromomelamine and mixtures thereof, and further including at least one formulation additive selected from the group consisting of a scale inhibitor, a clarifier, and an algaecide.

15. The tablet of claim 14, wherein the scale inhibitor is an organic phosphonate acid.

16. The tablet of claim 14, wherein the clarifier is ethylene diamine tetra acetic acid.

17. The tablet of claim 14, wherein the algaecide is selected from the group consisting of copper sulfate and a quaternary ammonium compound.

18. The tablet of claim 14, wherein the halogen source includes one mole of trichloroisocyanuric and four moles of sodium dichloroisocyanuric acid.

19. The tablet of claim 14, wherein the halogen source includes one mole of trichloroisocyanuric and four moles of potassium dichloroisocyanuric acid.

20. A solid, multi-layer water treatment tablet comprising, sequentially, one discrete layer comprising at least one halogen source and a second discrete layer comprising an inert boundary layer and a third layer comprising at least one pH compensating source, said first and third layers each being configured to be simultaneously exposed to an aqueous solution and wherein the boundary layer comprises a material selected from the group consisting of alkali metal chlorides, alkali metal phosphates, alkali silicates, alkali borates and alkali metal sulfates.

21. A solid, multi-layer water treatment tablet comprising, sequentially, one discrete layer comprising at least one halogen source and a second discrete layer comprising an inert boundary layer and a third layer comprising at least one pH compensating source, said first and third layers each being configured to be simultaneously exposed to an aqueous solution and wherein the halogen source is acidic in aqueous solution and the pH compensating source is basic in aqueous solution, wherein the halogen source is selected from the group consisting of trichloroisocyanuric acid, dichloroisocyanuric acid, monochloroisocyanuric acid, potassium dichloroisocyanuric acid, sodium dichloroisocyanuric acid dihyrate, anhydrous sodium dichloroisocyanuric acid, tribromoisocyanuric acid, dibromoisocyanuric acid, monobromoisocyanuric acid, monobromodichloroisocyanuric acid, dibromo-monochloroisocyanuric acid, 1,3-dichloro-5,5-dimethylhydantoin, 1,3-dibromo 5,5-dimethylhydantoin, 1-bromo-3-chloro-5,5-dimethylhydantoin, 1,3-dichloro-5-methyl-5-ethylhydantoin, 1,3-dichloro-5, 5-dimethylhydantoin, 1,3-dibromo-5,5-dimethylhydantoin, trichloromelamine, tribromomelamine and mixtures thereof, and further including at least one formulation additive selected from the group consisting of a scale inhibitor, a clarifier, and an algaecide.

22. The tablet of claim 21, wherein the scale inhibitor is an organic phosphonate acid.

23. The tablet of claim 21, wherein the clarifier is ethylene diamine tetra acetic acid.

24. The tablet of claim 21, wherein the algaecide is selected from the group consisting of copper sulfate and a quaternary ammonium compound.

25. A solid, multi-layer water treatment tablet comprising, sequentially, one discrete layer comprising at least one halogen source and a second discrete layer comprising an inert boundary layer and a third layer comprising at least one pH compensating source, said first and third layers each being configured to be simultaneously exposed to an aqueous solution and wherein the halogen source is acidic in aqueous solution and the pH compensating source is basic in aqueous solution, wherein the pH compensating source includes sodium bicarbonate, and further including at least one formulation additive selected from the group consisting of a scale inhibitor, a clarifier, and an algaecide.

26. The tablet of claim 25, wherein the scale inhibitor is an organic phosphonate acid.

27. The tablet of claim 25, wherein the clarifier is ethylene diamine tetra acetic acid.

28. The tablet of claim 25, wherein the algaecide is selected from the group consisting of copper sulfate and a quaternary ammonium compound.

29. The tablet of claim 25, wherein the halogen source comprises one mole of trichloroisocyanuric and four moles of sodium dichloroisocyanuric acid.

30. The tablet of claim 25, wherein the halogen source comprises one mole of trichloroisocyanuric and four moles of potassium dichloroisocyanuric acid.

31. The tablet of claim 25, wherein the halogen source comprises about 60% by weight 1-bromo-3-chloro-dimethylhydantoin, about 30% by weight 1,3-dichloro-5,5-dimethylhydantoin and about 10% by weight 1,3-dichloro-5-ethyl-5-methylhydantoin.

32. A method of treating a water system, which comprises adding to the water a solid, multi-layer water treatment tablet comprising one discrete layer containing at least one halogen source and a second discrete layer containing at least one pH compensating source, said layers each being configured to be simultaneously exposed to an aqueous solution and wherein the halogen source is acidic in an aqueous solution and the pH compensating source is basic in an aqueous solution, wherein the halogen source is selected from the group consisting of trichloroisocyanuric acid, dichloroisocyanuric acid, monochloroisocyanuric acid, potassium dichloroisocyanuric acid, sodium dichloroisocyanuric acid dihyrate, anhydrous sodium dichloroisocyanuric acid, tribromoisocyanuric acid, dibromoisocyanuric acid, monobromoisocyanuric acid, monobromodichloroisocyanuric acid, dibromomonochloroisocyanuric acid, 1,3-dichloro-5, 5-dimethylhydantoin, 1,3-dibromo 5,5-dimethylhydantoin, 1-bromo-3-chloro-5,5-dimethylhydantoin, 1,3-dichloro-5-methyl-5-ethylhydantoin, 1,3-dichloro-5,5-dimethylhydantoin, 1,3-dibromo-5,5-dimethylhydantoin, 1,3-dibromo-5,5-dimethylhydantoin trichloromelamine, tribromomelamine and mixtures thereof, further including at least one formulation additive selected from the group consisting of a scale inhibitor, a clarifier, and an algaecide.

33. The method of claim 32, wherein the scale inhibitor is an organic phosphonate acid.

34. The method of claim 32, wherein the clarifier is ethylene diamine tetra acetic acid.

35. The method of claim 32, wherein the algaecide is selected from the group consisting of copper sulfate and a quaternary ammonium compound.

36. The method of claim 32, wherein the halogen source comprises one mole of trichloroisocyanuric and four moles of sodium dichloroisocyanuric acid.

37. The method of claim 32, wherein the halogen source comprises one mole of trichloroisocyanuric and four moles of potassium dichloroisocyanuric acid.

38. The method of claim 32, wherein the halogen source comprises about 60% by weight 1-bromo-3-chlorodimethylhydantoin, about 30% by weight 1,3 dichloro 5,5 dimethylhydantoin and about 10% by weight 1,3-dichloro-5-ethyl-5-methylhydantoin.

39. The method of claim 32, wherein the halogen source includes one mole of trichloroisocyanuric and four moles of sodium dichloroisocyanuric acid.

* * * * *